(12) United States Patent
Yamada et al.

(10) Patent No.: US 8,323,943 B2
(45) Date of Patent: Dec. 4, 2012

(54) SCREENING METHOD FOR ANTICANCER DRUG

(75) Inventors: Tesshi Yamada, Tokyo (JP); Miki Shitashige, Tokyo (JP); Setsuo Hirohashi, Tokyo (JP)

(73) Assignee: National Cancer Center, Tokyo (JP)

( * ) Notice: Subject to any disclaimer, the term of this patent is extended or adjusted under 35 U.S.C. 154(b) by 872 days.

(21) Appl. No.: 12/191,049

(22) Filed: Aug. 13, 2008

(65) Prior Publication Data

US 2009/0215081 A1    Aug. 27, 2009

(30) Foreign Application Priority Data

Feb. 21, 2008 (JP) ................................. 2008-039618

(51) Int. Cl.
*G01N 33/573* (2006.01)
*G01N 33/53* (2006.01)
*G01N 33/566* (2006.01)
*C12Q 1/48* (2006.01)
*C12N 9/12* (2006.01)

(52) U.S. Cl. .............. 435/194; 435/4; 435/7.1; 435/7.4; 435/15; 435/971; 436/501; 436/63; 436/64

(58) Field of Classification Search .............. 435/4, 194, 435/7.1, 7.4, 15, 971; 436/501, 63, 64
See application file for complete search history.

(56) References Cited

U.S. PATENT DOCUMENTS 6,514,719 B1 * 2/2003 Bird et al. ....................... 435/15
7,250,488 B1   7/2007 Akiyama et al.

FOREIGN PATENT DOCUMENTS

WO         00/64933        11/2000

OTHER PUBLICATIONS

Hao, W.H., et al. Journal of Biological Chemistry, 261(6): 3075-3084, 2006.*
Chadee, D.N., et al., Molecular and Cellular Biology, 22(3): 737-749, 2002.*
Federov, O. et al, Proceedings of the National Academy of Sciences, 104(510: 20523-20528, Dec. 2007.*
Fu et al., "TNIK, A Novel Member of the Germinal Center Kinase Family That Activates the c-Jun N-terminal Kinase Pathway and Regulates the Cytoskeleton," The Journal of Biological Chemistry, vol. 274, No. 43, pp. 30729-30737, Oct. 22, 1999.
Luciferase reporter Top-Flash, and Fop-Flash (Millipore Co.) (http://www.millipore.com/catalogue/item/21-169, and http://www.millipore.com/catalogue/item/21-170), printed Aug. 13, 2008.
Supplementary European Search Report in Application No. EP 09 71 3312, completed Jun. 22, 2011.
Leporcelet M. et al.: "Small-molecule antagonists of the oncogenic Tcf/beta-catenin protein complex," Cancer Cell, vol. 5, No. 1, Jan. 1, 2004 , pp. 91-102, XP002984831, *see in particular the paragraphs "Introduction" and "Experimental procedures"*.
Shitashige M. et al.: "Wnt signaling inside the nucleus", Cancer Sci., vol. 99, No. 4, Apr. 2008, pp. 631-637, XP002644394, [retrieved on Jan. 2, 2008] *table 1* *p. 635*.
Shitashige M. et al.: "Traf2- and Nck-interacting kinase is essential for Wnt signaling and colorectal cancer growth", Cancer Res. vol. 70, No. 12, Jun. 15, 2010, pp. 5024-5033, XP002644395, [retrieved on Jun. 8, 2010].
Mahmoudi T. et al.: "The kinase TNIK is an essential activator of Wnt target genes", EMBO J., vol. 28, No. 21, Nov. 4, 2009, pp. 3329-3340, XP002644396, [retrieved on Oct. 8, 2009].

* cited by examiner

*Primary Examiner* — Alana Harris Dent
*Assistant Examiner* — Anne Holleran
(74) *Attorney, Agent, or Firm* — Griffin & Szipl, P.C.

(57) ABSTRACT

The screening method for an anticancer drug comprises selecting a compound which blocks the kinase activity of TNIK, or blocks the combination of TNIK with β-catenin/TC4 transcription complex.

9 Claims, 9 Drawing Sheets

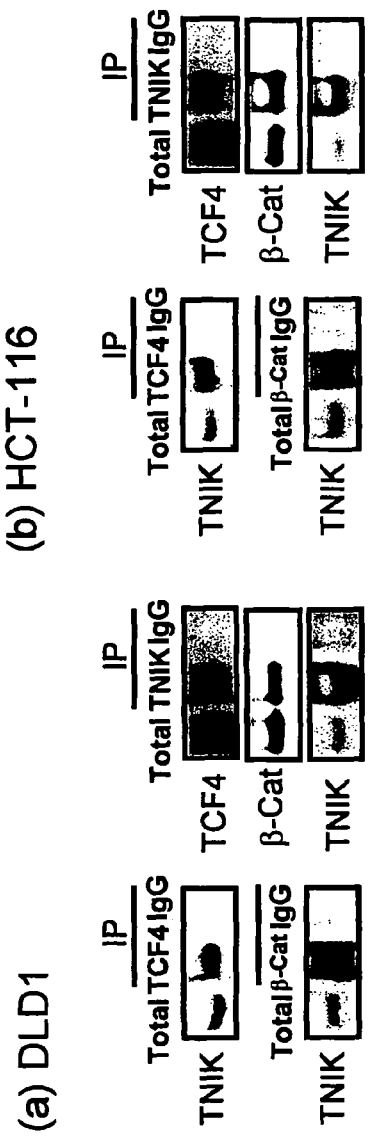
FIG.1 Endogenous interaction between TRAF2 and NCK interacting kinase (TNIK) with β-catenin/TCF4 complex

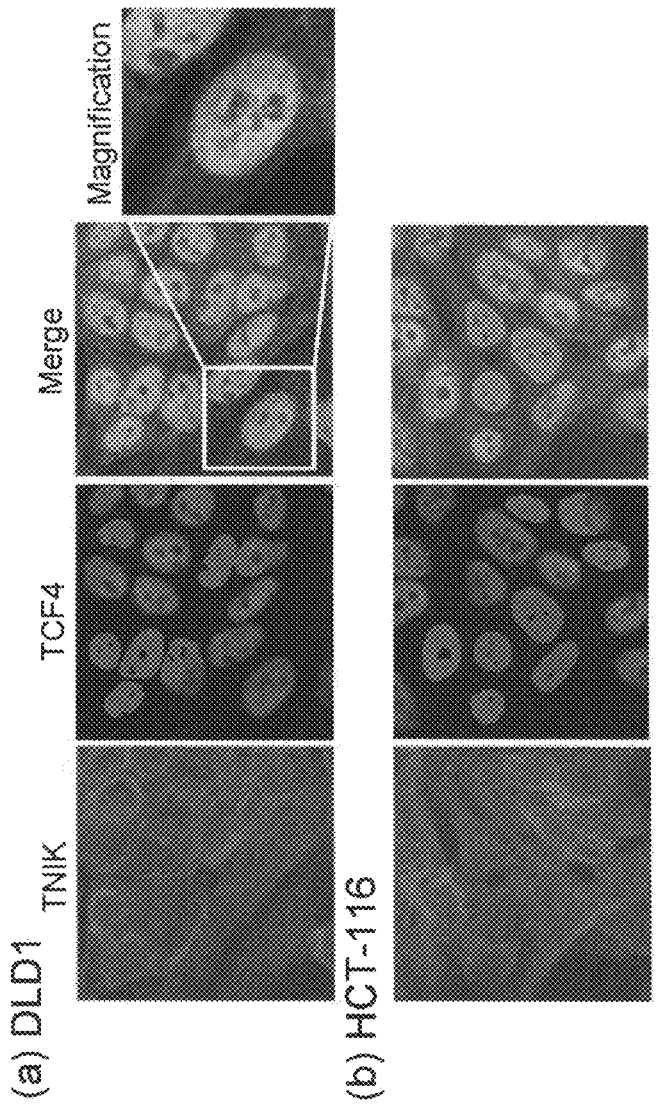
FIG.2 Immunofluorescence-stain images showing the localization of TNIK and TCF4 in DLD-1 cells and HCT-116 cells

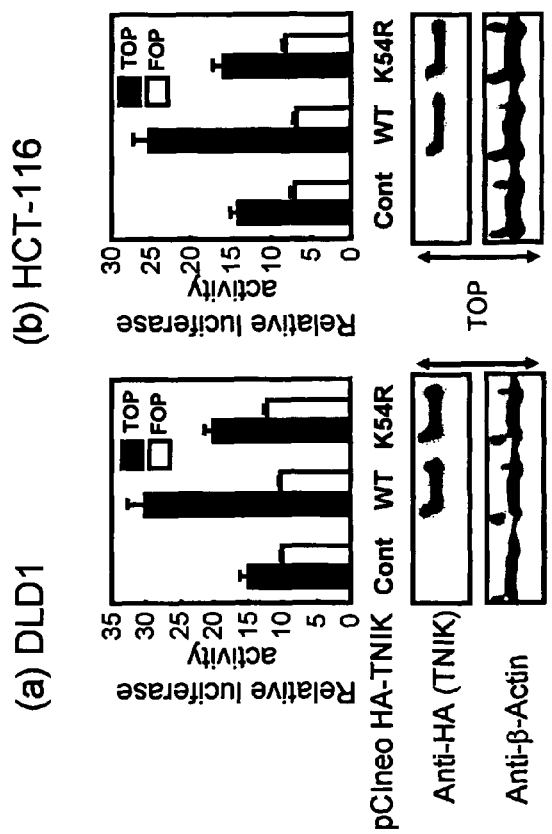
FIG.3 Increased transcriptional activity of β-catenin/TCF4 complex due to TNIK

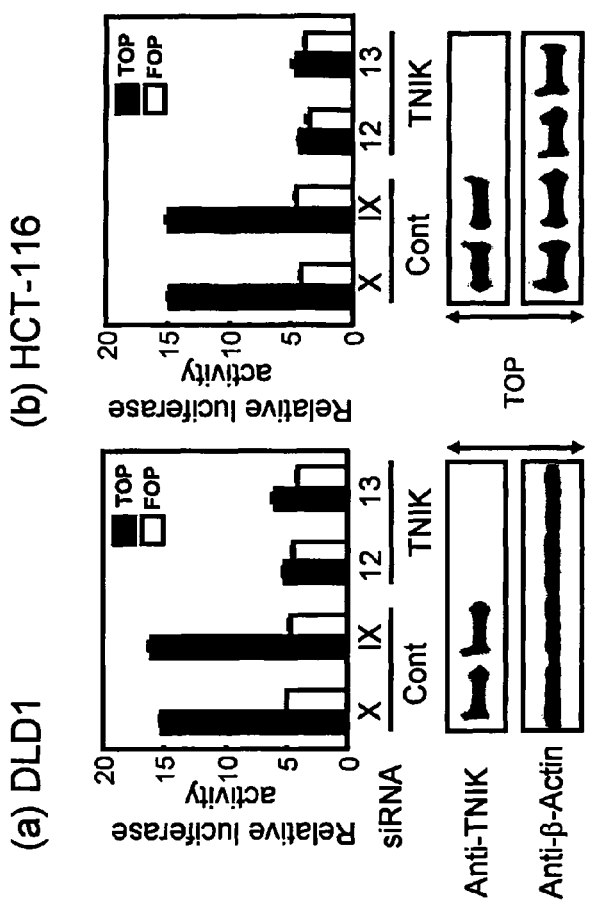
FIG.4 Inhibition of transcriptional activity of β-catenin/TCF4 complex due to knockdown of TNIK

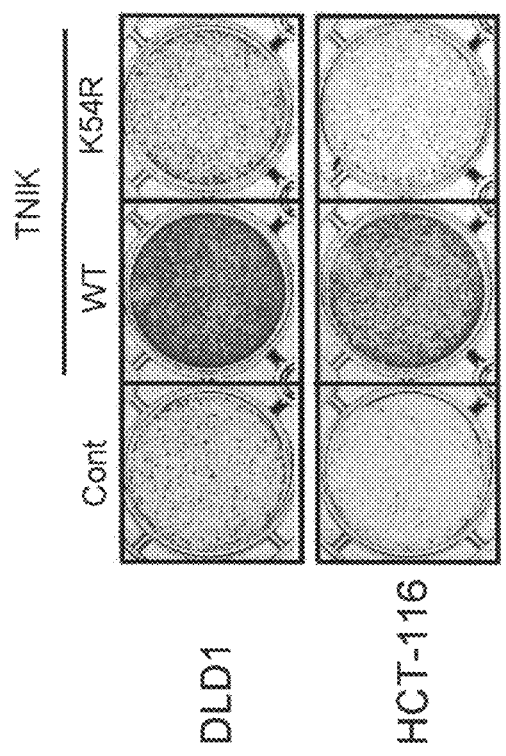
FIG. 5 Proliferation increase of colon cancer cells due to TNIK

FIG. 6 Inhibition of proliferation of colon cancer cells due to knockdown of TNIK
(a) DLD1
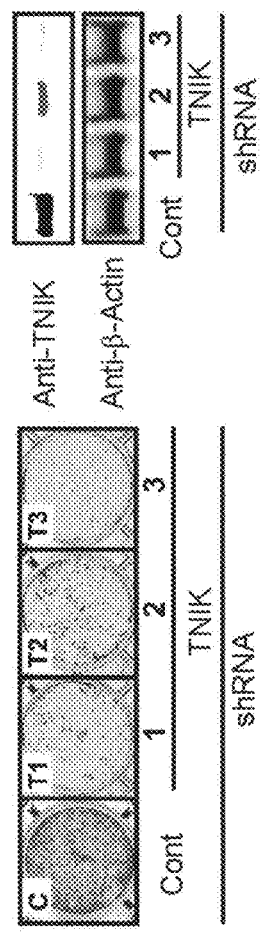
(b) HCT-116
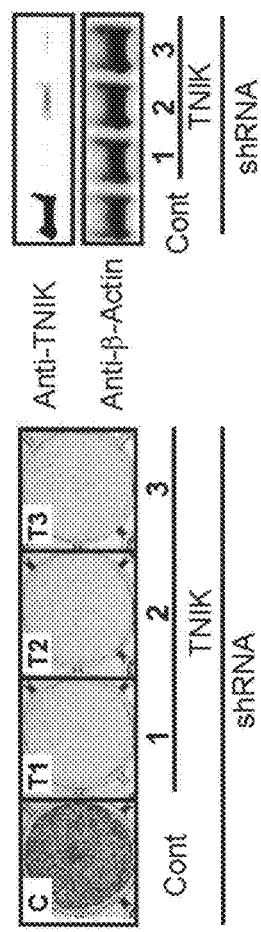

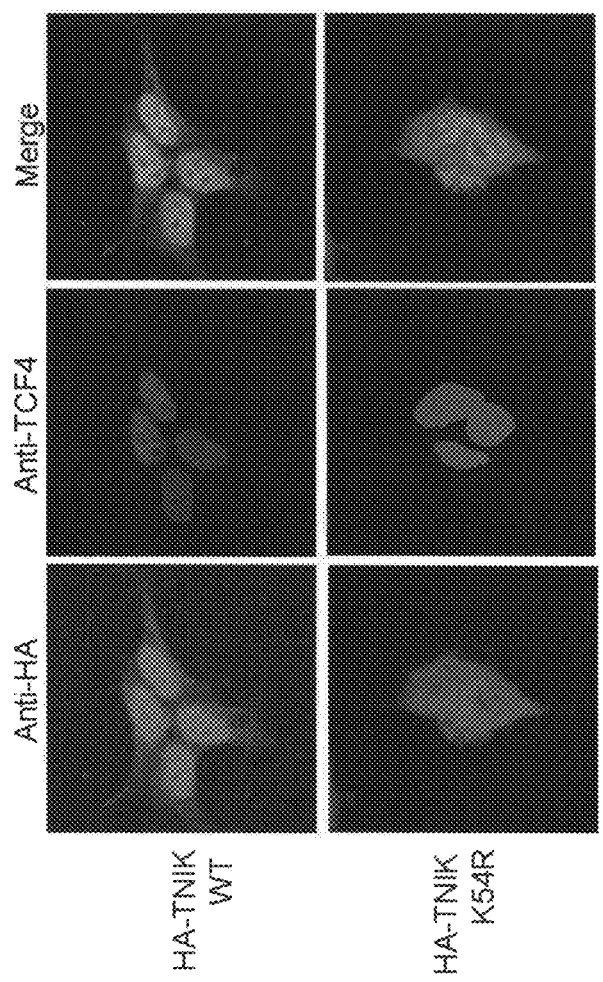
FIG.7 Nuclear localization incompetence of ATP binding site mutant TNIK (K54R)

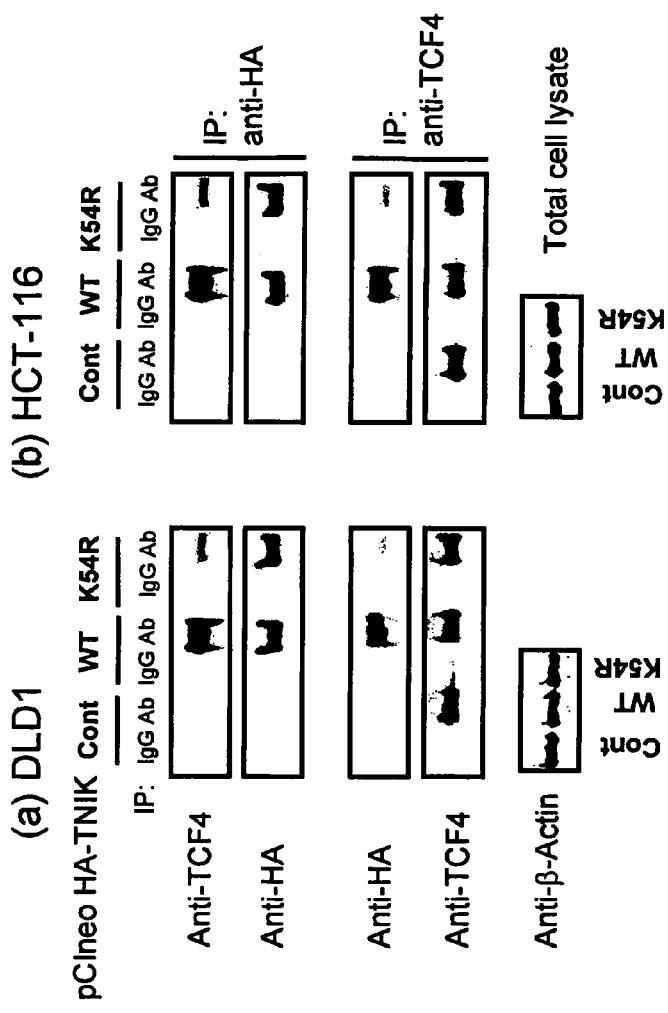
FIG.8 TCF4 interaction incompetence of ATP binding site mutant TNIK (K54R)

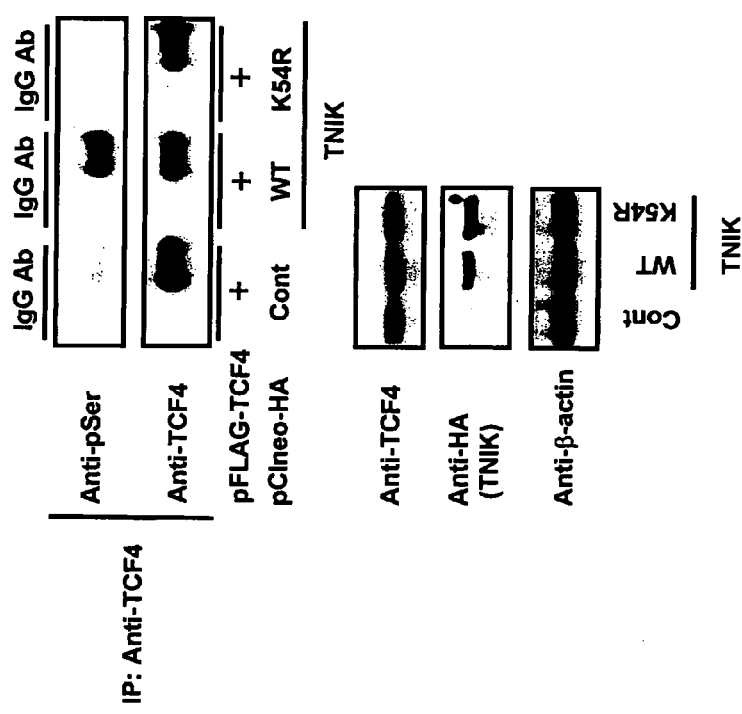
FIG.9 Phosphorylation of TCF4 by TNIK

SEQUENCE LISTING

```
<160> NUMBER OF SEQ ID NOS: 8

<210> SEQ ID NO 1
<211> LENGTH: 21
<212> TYPE: RNA
<213> ORGANISM: Artificial Sequence
<220> FEATURE:
<223> OTHER INFORMATION: Sense strand for siRNA

<400> SEQUENCE: 1
cgacauaccc agacugauau u                                             21

<210> SEQ ID NO 2
<211> LENGTH: 21
<212> TYPE: RNA
<213> ORGANISM: Artificial Sequence
<220> FEATURE:
<223> OTHER INFORMATION: Antisense strand for siRNA
<220> FEATURE:
<221> NAME/KEY: modified base
<222> LOCATION: (1)..(1)
<223> OTHER INFORMATION: Phosphorylated uracil

<400> SEQUENCE: 2
naucagucug gguaugucgu u                                             21
```

```
<210> SEQ ID NO 3
<211> LENGTH: 21
<212> TYPE: RNA
<213> ORGANISM: Artificial Sequence
<220> FEATURE:
<223> OTHER INFORMATION: Sense strand for siRNA

<400> SEQUENCE: 3
gaccgaagcu cuugguuacu u                                              21

<210> SEQ ID NO 4
<211> LENGTH: 21
<212> TYPE: RNA
<213> ORGANISM: Artificial Sequence
<220> FEATURE:
<223> OTHER INFORMATION: Antisense strand for siRNA
<220> FEATURE:
<221> NAME/KEY: modified base
<222> LOCATION: (1)..(1)
<223> OTHER INFORMATION: Phosphorylated guanine

<400> SEQUENCE: 4
nuaaccaaga gcuucggucu u                                              21

<210> SEQ ID NO 5
<211> LENGTH: 21
<212> TYPE: DNA
<213> ORGANISM: Artificial Sequence
<220> FEATURE:
<223> OTHER INFORMATION: Insert sequence designed for shRNA expression

<400> SEQUENCE: 5
acacactggt ttccatgtaa t                                              21

<210> SEQ ID NO 6
<211> LENGTH: 21
<212> TYPE: DNA
<213> ORGANISM: Artificial Sequence
<220> FEATURE:
<223> OTHER INFORMATION: Insert sequence designed for shRNA expression

<400> SEQUENCE: 6
agagaaggaa ccttgatgat t                                              21

<210> SEQ ID NO 7
<211> LENGTH: 21
<212> TYPE: DNA
<213> ORGANISM: Artificial Sequence
<220> FEATURE:
<223> OTHER INFORMATION: Insert sequence designed for shRNA expression

<400> SEQUENCE: 7
agaaagattt cggtggtaaa t                                              21

<210> SEQ ID NO 8
<211> LENGTH: 21
<212> TYPE: DNA
<213> ORGANISM: Artificial Sequence
<220> FEATURE:
<223> OTHER INFORMATION: Insert sequence designed for shRNA expression

<400> SEQUENCE: 8
ggaatctcat tcgatgcata c                                              21
```

SCREENING METHOD FOR ANTICANCER DRUG

This application claims priority from Japanese Patent Application No. 2008-039618, filed Feb. 21, 2008, the entire disclosure of which is incorporated herein by reference.

FIELD OF THE INVENTION

The present invention relates to a screening method for an anticancer drug effective in cancers in which β-catenin participates, and more specifically to a method of screening an anticancer drug effective in cancers in which β-catenin participates by controlling the function of β-catenin/TCF4 transcription complex.

BACKGROUND OF THE INVENTION

A mutation in the APC (adenomatous polyposis coli) antioncogene, which has been identified as a genetic cause of familial adenomatous polyposis, is a mutation which takes place early in the oncogenic pathways of not only familial adenomatous polyposis but also of sporadic colon cancer, and it is a very common genetic mutation seen in more than 80% of cases.

It is known that a mutation of this APC antioncogene leads to the intracellular accumulation of β-catenin. This β-catenin combines with a transcription factor of the TCF/LEF family, and leads to transcriptional activity. In many cases of colon cancer, in the TCF/LEF family, cell biology changes arise in the intestinal epithelium due to the transcriptional activation of T-cell factor-4 (TCF4) which affects the control of differentiation of the intestinal epithelium. It is thought that, subsequently, this forms an early colon adenoma and results in oncogenic transformation through a secondary multi-stage genetic mutation.

Since a mutation of the β-catenin gene is seen in about half of the cases wherein there is no genetic mutation of APC, compounds which inhibit the function of the transcription complex of β-catenin and TCF4 (β-catenin/TCF4 transcription complex) are viewed as a promising a new molecular therapeutic drug for colon cancer.

In this context, therapeutic drugs that, by binding with β-catenin, have an inhibitory action on transcriptional activation when β-catenin combines with TCF/LEF family proteins to form complexes, have been proposed (Patent document 1). Patent document 1: International publication 00/No. 64933

However, a satisfactory effective compound had not yet been developed, and it was therefore desired to develop an effective molecular therapy for colon cancer.

SUMMARY OF THE INVENTION

It is therefore a purpose of the present invention to provide a screening method for discovering an anticancer drug effective in cancers in which β-catenin participates by inhibiting the function of β-catenin/TCF4 transcription complex.

The Inventors, after intensive studies to achieve the above purpose, discovered that TRAF2 and NCK interacting kinase (TNIK) is an enzyme that affects the phosphorylation of TCF4 (T-cell factor-4), and that this enzyme interacts functionally with β-catenin/TCF4 transcription complex, and contributes to the abnormal transcriptional activation of TCF4 seen in colon cancer.

The Inventors also found that, by interfering with the kinase activity of TNIK, or interfering with the combination of TNIK and β-catenin/TCF4 transcription complex, the function of β-catenin/TCF4 transcription complex is inhibited, and the oncogenic transformation of the cells can be stopped. Also, by selecting a compound that blocks the kinase activity of TNIK, or blocks the combination of TNIK and β-catenin/TCF4 transcription complex, it is possible to screen for an anticancer drug effective in cancers in which β-catenin participates.

The present invention is therefore a screening method for an anticancer drug characterized by selecting a compound that blocks the kinase activity of TNIK, or blocks the combination of TNIK and β-catenin/TCF4 transcription complex (first embodiment).

The screening method of the present invention comprises a step for selecting a compound that blocks the binding of ATP to the ATP binding site of TNIK (second embodiment). This may be a method that comprises a step of selecting a candidate compound based on the conformation of the ATP binding site of TNIK (third embodiment).

The candidate compound for an anticancer drug may be a compound such that, when the kinase activity of TNIK in the presence of the candidate compound is measured, the kinase activity of TNIK in the presence of the candidate compound is lower than in its absence (fourth embodiment).

According to the screening method of the invention, the intensity of the interaction of β-catenin/TCF4 transcription complex and TNIK is measured in the presence of a candidate compound, the candidate compound being selected when the interaction between β-catenin/TCF4 transcription complex and TNIK in the presence of the candidate compound is less than in its absence (fifth embodiment). In this case, it is preferred to measure this interaction using a two-hybrid assay (sixth embodiment) or an antigen-antibody reaction (seventh embodiment). Also, in the screening method of the invention, cells which express β-catenin, TCF4, and TNIK are cultured in the presence of a candidate compound, the candidate compound being selected when cell proliferation is inhibited more in the presence of the candidate compound than in its absence (eighth embodiment).

The screening method of the invention is useful in order to screen an anticancer drug that is especially effective in colon cancer (ninth embodiment).

EFFECT OF THE INVENTION

According to the present invention, by selecting a compound that blocks the kinase activity of TNIK, or by selecting a compound that interferes with the combination of TNIK and β-catenin/TCF4 transcription complex, it is possible to screen for an anticancer drug before an experiments using animals, that is effective in cancers in which β-catenin participates with a high probability of effectiveness.

BRIEF DESCRIPTION OF THE DRAWINGS

FIG. 1 is a set of diagrams showing an endogenous interaction between TRAF2 and NCK interacting kinase (TNIK) with β-catenin/TCF4 complex.

FIG. 2 is a set of immunofluorescence-stain images showing the localization of TNIK and TCF4 in DLD-1 cells and HCT-116 cells.

FIG. 3 is a set of diagrams showing the increase of transcriptional activity of β-catenin/TCF4 complex due to TNIK. (a) DLDI Relative liciferase activity and (b) HCT-116 Relative liciferase activity FIG. 4 is a set of diagrams showing inhibition of the transcriptional activity of β-catenin/TCF4 complex due to knockdown of TNIK.

(a) DLDI Relative liciferase activity and (b) HCT-116 Relative liciferase activity FIG. 5 is a set of diagrams showing a proliferation increase of colon cancer cells due to TNIK.

FIG. 6 is a set of diagrams showing an inhibition of proliferation of colon cancer cells due to knockdown of TNIK.

FIG. 7 is a set of images showing a nuclear localization incompetence of an ATP binding site mutant TNIK (K54R).

FIG. 8 is a set of diagrams showing a TCF4 interaction incompetence of ATP binding site mutant TNIK (K54R).

FIG. 9 is a diagram showing a phosphorylation of TCF4 by TNIK.

DESCRIPTION OF THE PREFERRED EMBODIMENTS

Hereafter, a screening method for an anticancer drug effective in cancers in which β-catenin participates according to the invention will be described in detail.

One aspect of the screening method of the invention is a method of selecting a compound that blocks the kinase activity of TNIK.

TRAF2/NCK interacting kinase(TRAF2 and NCK interacting kinase: TNIK) is an enzyme for phosphorylation identified as a germinal center kinase (GCK) that activates the c-Jun N-terminal kinase (JNK) signalling pathway which is activated by a wide range of stress stimulations (Fu et al., J. Biol. Chem. 274: 30729-30737, 1999).

This TNIK is an enzyme that affects the phosphorylation of TCF4, and it activates the transcription of TCF4 by functionally interacting with β-catenin/TCF4 transcription complex. Therefore, if the kinase activity of this TNIK can be blocked, it would be possible to inhibit the transcriptional activation of TCF4.

In order to reduce the huge cost, and labor, etc. which are required for selection of compounds that block the kinase activity of TNIK, in the present invention, it is desirable to extract compounds that block the kinase activity of TNIK beforehand using computer technology. For example, compounds that block the kinase activity of TNIK, or compounds that interfere with the binding of ATP to the ATP binding site of TNIK, may be extracted beforehand as candidate compounds using computer technology. Specifically, using bioinformatics technology, compounds having a chemical structure which potentially interfere with the binding of ATP to the ATP binding site of TNIK may be selected from those known in the art, or may be newly designed based on the conformation of the ATP binding site of TNIK. When selecting from among publicly known compounds, information such as a self-made compound library or an existing compound library acquired via the Internet, may also be used.

As another positive method of selecting a compound that blocks the kinase activity of TNIK, there is also a method whereby the kinase activity of TNIK in the presence of the candidate compound is measured, the compound being selected when the measured kinase activity is lower than the kinase activity in its absence.

"Candidate compound" in the context of this specification is a concept which means all the compounds which might be a candidate for an anticancer drug, and includes not only publicly known compounds but also new designer compounds.

Measurement of the kinase activity of TNIK in the invention can be performed by measuring the phosphorylating ability of TNIK.

The method of measuring the phosphorylating ability of TNIK is not particularly limited, but for example may be an in vitro kinase assay or an in vivo kinase assay.

In an in vitro kinase assay, an enzyme that is a recombinant protein and ATP are mixed in a test tube. A phosphorylation reaction is performed by incubating with a substrate which is a recombinant protein, and the degree of phosphorylation of the substrate is determined.

In the invention, after performing a phosphorylation reaction using TNIK as the enzyme, and using β-catenin/TCF4 transcription complex as the substrate, the degree of phosphorylation of the β-catenin/TCF4 transcription complex is determined. The method of determining the degree of phosphorylation includes a method of using radioactive ATP or nonradioactive ATP. When $^{32}P$ radioactive labelled ATP is used as the ATP, the $^{32}P$ radioactivity taken into the substrate is measured. When nonradioactive ATP is used, the degree of phosphorylation of β-catenin/TCF4 transcription complex can be determined by performing Western blot or the like using a phosphorylation antibody.

In vivo kinase assay is a method of determining, in cells, the degree of phosphorylation of an endogenous substrate or a substrate which is over-expressed by an endogenous enzyme or an over-expressed enzyme.

In the invention, after performing a phosphorylation reaction by endogenous ATP and separating a substrate by immunoprecipitation, the degree of phosphorylation can be determined by performing Western blot or the like on the obtained immunoprecipitation using a phosphorylation antibody. It can also be measured by adding $^{32}P$ radioactive labelled ATP to a culture liquid, culturing cells, separating the substrate by immunoprecipitation or the like, and measuring the $^{32}P$ radioactivity.

Another aspect of the screening method of the invention is a screening method for an anticancer drug which selects a compound which blocks the combination of β-catenin/TCF4 transcription complex and TNIK.

TNIK combines with β-catenin/TCF4 transcription complex, and its functional interaction with β-catenin/TCF4 transcription complex activates transcription of TCF4. Therefore, if the combination of TNIK and β-catenin/TCF4 transcription complex could be blocked, it would be possible to inhibit the transcriptional activation of TCF4.

As one aspect of a method of selecting a compound which blocks combination of β-catenin/TCF4 transcription complex and TNIK, the degree of interaction between β-catenin/TCF4 transcription complex and TNIK is measured in the presence of the candidate compound, and a compound for which the measured interaction between β-catenin/TCF4 transcription complex and TNIK is lower than in its absence is selected as an anticancer drug.

The method of measuring the degree of interaction between β-catenin/TCF4 transcription complex and TNIK is not particularly limited provided that this degree can be measured, but a reporter assay, a two-hybrid assay, and an antigen-antibody reaction or the like may for example be given.

According to the two-hybrid assay, the interaction between proteins can be measured using the fact that if they combine, it will give rise to transcription factor activity even if the DNA binding site of the transcription factor and the transcription activation site are on different molecules, and this can be done using either budding yeast cells or mammalian cells. When a protein A to be examined is bound to the DNA binding site of a transcription factor, another protein B is bound to the transcription activation site and introduced into cells and a reporter assay is performed, the DNA binding transcription factor is reconstructed by the combination of protein A and protein B inside the cells. As a result, since the genes of the enzyme derived from the reporter are expressed, the interaction between protein A and protein B can be detected.

The two-hybrid assay which is used in the present invention is a commonly used method, and is not particularly limited. For example, the cDNA construct which expresses the recombinant protein of the DNA binding site of a transcription factor and TNIK, the cDNA construct which expresses the recombinant protein of a transcriptional activation site and β-catenin/TCF4 transcription complex, and the cDNA construct which expresses a reporter due to the action of this transcriptional activation site, are simultaneously introduced in a cell. Since the reporter gene is expressed by the action of the transcription active site when β-catenin/TCF4 transcription complex and TNIK are combined together, the degree of interaction can be measured by measuring the enzyme activity which is the expression product of the reporter gene. Of course, the cDNA construct which expresses the recombinant protein of the DNA binding site of the transcription factor and β-catenin/TCF4 transcription complex, and the cDNA construct which expresses the recombinant protein of the transcriptional activation site and TNIK, may also be used.

A "reporter gene" means a gene which can detect a gene expression product quantitatively, specifically a gene for which the nucleotide sequence and/or amino acid sequence of the gene are known, or a gene which can emit a signal (fluorescence, etc.) of which the intensity differs according to the amount of gene expression.

As a reporter gene, a luciferase gene, a CAT gene, a lacZ gene or the like may be mentioned, but according to the invention, it is particularly preferred to use a luciferase gene, such as a firefly luciferase gene and a renilla luciferase gene.

According to the invention, the reporter gene is introduced into cells, the enzyme amount expressed from the reporter gene is measured as described above, and compared with the enzyme amount measured by an identical method in the absence of the candidate compound, whereby an anticancer drug effective for cancers in which β-catenin participates can be effectively screened by selecting a compound for which the former enzyme amount is less than the latter enzyme amount.

According to the measurement method using an antigen-antibody reaction, for example, immunoprecipitation is performed using antibodies to TNIK from the extracts of cells expressing TNIK, β-catenin and TCF4. Next, a measurement can be made by performing an immunoblot analysis on the obtained precipitation using antibodies to β-catenin and/or TCF4. When a band showing a complex of TNIK-β-catenin or TNIK-TCF4 is obtained by this immunoblot analysis, the amount of protein contained in that band shows the degree of these interactions. After performing an immunoprecipitation using antibodies to β-catenin and/or TCF4, an immunoblot analysis may be performed using antibodies to TNIK.

According to the invention, cells which express TNIK, β-catenin, and TCF4 into which genes have been introduced are cultured in the presence of the candidate compound, immunoprecipitation and immunoblot analysis are performed by the aforesaid method, the degree of interaction is measured, and compared with the degree of interaction in the absence of the candidate compound. An anticancer drug effective in cancers in which β-catenin participates can then be selected by selecting a candidate compound for which this degree is less in the presence of the candidate compound than in its absence.

The cells which express TNIK, β-catenin, and TCF4 which are used in the invention may be commonly known colon cancer cells, such as not only those of humans but also those of mice and rats, however DLD-1, HCT-116, WiDr, are preferably used from the viewpoint that β-catenin is accumulated in the nucleus.

According to another aspect of selecting a compound which blocks the kinase activity of TNIK, or selecting a compound which blocks combination of β-catenin/TCF4 transcription complex and TNIK, a method may be mentioned wherein cells expressing β-catenin, TCF4 and TNIK are cultured in the presence of a candidate compound, and a candidate compound for which cell proliferation is inhibited compared to the case where the cells are cultured in the absence of the compound, is selected as an anticancer drug.

The Inventors found that the transcriptional activation of TCF4 can be inhibited by blocking the kinase activity of TNIK, or interfering with the combination of TNIK and β-catenin/TCF4 transcription complex. Therefore, an anticancer drug effective in cancers in which β-catenin participates can be selected by verifying whether cell proliferation is inhibited. The method of verifying inhibition of cell proliferation is not particularly limited, but for example, inhibition of cell proliferation may be verified by colony formation assay, the MTT [3-(4,5-dimethylthial-2-yl)-2,5-diphenyltetrazalium bromide] method, or counting the number of cells.

The aforesaid MTT method is a coloration detection method wherein MTT is added to a cell culture, and the number of living cells is analyzed by measuring the amount of added MTT that is decomposed. Specifically, when cells grown on a culture dish are incubated in a MTT solution, formazan pigment insoluble in water is produced mainly depending on the enzyme activity of the mitochondria. After solubilizing this formazan pigment, it is measured with a spectrophotometer.

Since the absorbance obtained is proportional to the number of living cells, the degree of cell growth can be measured relatively.

Examples of cancers in which β-catenin participates, which are the object of the screening method of the invention, include colon cancer, ovarian cancer, endometrial cancer, childhood brain tumor (medulloblastoma), liver cancer, hepatoblastoma and stomach cancer, but the invention is particularly useful as a screening method for anticancer drugs effective in colon cancer.

EXAMPLES

Hereafter, the invention will be described by way of specific examples, but it is not to be construed as being limited in any way thereby.

First, the samples, reagents, and experimental methods used in the examples of the invention will be described, but in the examples, unless otherwise specified, the experiments were performed according to the following methods.

(Cell Strain)

Human colon cancer cell strain DLD-1 was acquired from the human science research resource bank (Osaka), and human colon cancer cell strain HCT-116 was acquired from ATCC (American Type Culture Collection) (U.S.).

(Plasmid)

pCIneo-HA vector (Promega, Madison, Wis.) into which human TNIK full length cDNA had been introduced, and pCIneo-HA vector into which mutant TNIK (K54R), wherein the 54th lysine in the ATP binding site was replaced by arginine, had been introduced, were supplied by Dr. Ken-ichi Kariya (University of the Ryukyus) (Okinawa).

Full length cDNA of human TCF4 was obtained by subcloning with the pFLAG-CMV-4 vector (Sigma-Aldrich) (FLAG-TCF4).

These cDNA(s) were introduced into HCT-116 cells and DLD-1 cells using Lipofectamine 2000 (Invitrogen Co.).

(Antibody)

Anti-β-catenin (clone 14) monoclonal antibody was purchased from BD Biosciences Co. (Palo Alto, Calif.), and anti-TCF4 (6H5-3) monoclonal antibody was purchased from Upstate Co. (Charlottesville, Va.).

Anti-TNIK rabbit polyclonal antibody (GTX13141) was purchased from Gene Tex Co. (San Antonio, Tex.), and anti-TNIK monoclonal antibody (3D4) was purchased from Abnova Co. (Taipei, Taiwan).

Anti-TCF4 (sc-13027), anti-HA[hemagglutinin] (sc-805) rabbit polyclonal antibody, rabbit IgG, and mouse IgG were purchased from Santa Cruz Biotechnology Co. (Santa Cruz, Calif.).

Anti-phospho-serine rabbit polyclonal antibody (ab9332) was purchased from Abcam Co. (Cambridge, Mass.).

Anti-HA monoclonal antibody (12CA5) and anti-β-actin monoclonal antibody (AC-74) were purchased from Abgent Co. (San Diego, Calif.).

(Immunoprecipitation)

Cell extract extracted using the following Lysis Buffer, was incubated at 4° C. overnight together with anti-β-catenin monoclonal antibody, anti-TCF4 monoclonal antibody, anti-TNIK rabbit polyclonal antibody, anti-HA monoclonal antibody, mouse IgG, or rabbit IgG overnight, mixed with Dynabeads protein G (Dynal Biotech Co., Oslo, Norway), and incubated for a further 1 hour.

Then, they were precipitated magnetically, and separated by sodium dodecyl sulfate-polyacrylamide gel electrophoresis (SDS-PAGE).

Lysis Buffer: 50 mM Tris-HCl, pH 7.4, 150 mM NaCl, 1 mM $MgCl_2$, 1 mM $CaCl_2$, 1 mMEDTA, 0.5% Triton X100, 0.05% SDS, 2 mM TCEP, 1 mM PMSF, 10 mM NaF, protease inhibitor cocktail (Boehringer Mannheim Co., Indianapolis, Ind.), Phosphatase inhibitor cocktail 1 and 2 (SIGMA-Aldrich Co.).

(Immunoblot)

After the protein in the sample was separated by SDS-PAGE, it was transferred to Immobilon-P membranes (Millipore, Billerica Mass.). After incubating a transfer film with a primary antibody at 4° C. overnight and incubating with a secondary antibody for a further 1 hour, it was detected using ECL Western blotting detection reagents (Amersham Biosciences, Amersham, UK).

(Immunofluorescence-Stain Method)

DLD-1 cultured cells and HCT-116 cultured cells were fixed on a cover glass by treating for 10 minutes with 4% paraformaldehyde, and the permeability of the cell membrane was enhanced by treating for 10 minutes with 0.2% Triton X-100. Then, the cells which had been fixed on the cover glass were incubated together with anti-TNIK rabbit polyclonal antibody or anti-TCF4 monoclonal antibody and anti-HA rabbit polyclonal antibody at 4° C. for 1 hour. After incubating the obtained cells with Alexa 594 anti-mouse IgG antibody and Alexa 488 anti-rabbit IgG antibody (Invitrogen Co., Carlsbad, Calif.) as secondary antibodies for 1 hour, they were observed using a confocal laser scanning microscope (LSM5 PASCAL Co., Carl Zeiss, Jena, Germany).

(TCF/Lymphoid Enhancer factor (LEF) Reporter Assay)

Luciferase reporter TOP-FLASH, and FOP-FLASH (Millipore Co.) (http://www.millipore.com/catalogue/item/21-169, and http://www.millipore.com/catalogue/item/21-170), were used for evaluation of TCF/LEF transcriptional activity. A firefly luciferase reporter (TOP-FLASH or FOP-FLASH) plasmid, and renilla luciferase phRG-TK (Promega) plasmid as internal standard, were introduced into DLD-1 cells and HCT-116 cells using Lipofectamine 2000 (Invitrogen Co.). The experiment was repeated 3 times. After 24 hours in a gene expression system (FIG. 3) and 48 hours in an expression inhibition system (FIG. 4), according to the manufacturer's protocol, the cells were solubilized using the Lysis solution supplied with the kit.

Next, firefly luciferase activity was measured with renilla luciferase as an internal standard using a Dual-luciferase Reporter Assay system (Promega Inc, Madison, Wis.).

(RNA Interference)

TNIK-12 and TNIK-13, which are two kinds of oligo RNA siRNA (small interfering ribonucleic acids) interfering with TNIK, and control siRNA, were purchased from Dharmacon Co. (Chicago, Ill.). In TNIK-12, a sense strand is 5'-CGA-CAUACCCAGACUGAUAUU-3' [SEQ ID NO: 1], and an antisense strand is 5'-PUAUCAGUCUGGGUAUGUCGUU-3' [SEQ ID NO: 2].

In TNIK-13, a sense strand is 5'-GACCGAAGCUCUUG-GUUACUU-3' [SEQ ID NO: 3], and an antisense strand is 5'-PGUAACCAAGAGCUUCGGUCUU-3' [SEQ ID NO: 4]. Here, "P" in the aforesaid arrangement represents a phosphate group. Therefore, as for the nucleotide sequence expressed by SEQ ID NO: 2 and SEQ ID NO: 4, the residue at the 5' end is phosphorylated.

TNIK-1, TNIK-2, TNIK-3, which are three kinds of short hairpin ribonucleic acids (shRNA) plasmids for the TNIK incorporated in the pGeneClip vector, and control shRNA, were purchased from SuperArray Bioscience Corporation (Frederick, Md.).

In TNIK-1, the insert sequence is ACACACTGGTTTC-CATGTAAT [SEQ ID NO: 5], in TNIK-2, the insert sequence is AGAGAAGGAACCTTGATGATT [SEQ ID NO: 6], in TNIK-3, the insert sequence is AGAAAGATTTCGGTGG-TAAAT [SEQ ID NO: 7], and in control shRNA, the insert sequence is GGAATCTCATTCGATGCATAC [SEQ ID NO: 8].

These siRNA(s) and shRNA(s) were introduced into DLD-1 cells and HCT-116 cells using Lipofectamine 2000 (Invitrogen Co.).

(Colony Formation Assay)

To culture media of DLD-1 cells and culture media of HCT-116 cells on which transfection had been performed, 300 μg/ml and 1000 μg/ml of Geneticin G418 (Invitrogen Co.) were respectively added 24 hours after transfection, and the cells were cultured for 8 days. They were then stained using Gimza solution (Wako, Osaka, Japan).

Example 1

(Combination of β-catenin/TCF4 Transcription Complex and TNIK in a Colon Cancer Cell Strain)

On cell extracts of DLD-1 cells and HCT-116 cells which are colon cancer cells, immunoprecipitation was performed using anti-TNIK rabbit polyclonal antibody, normal rabbit IgG, anti-TCF4 monoclonal antibody, anti-β-catenin monoclonal antibody, or normal mouse IgG (IgG). On the precipitation (IP) and the cell extracts (Total), an immunoblot was performed using anti-TNIK rabbit polyclonal antibody, anti-TCF4 monoclonal antibody, and anti-β-catenin monoclonal antibody.

The result of the immunoblot is shown in FIG. 1. TNIK did undergo immunoprecipitation due to anti-TCF4 antibody, but did not precipitation with the control IgG.

TNIK also underwent immunoprecipitation due to the antibody to β-catenin (anti-β-catenin antibody) which is a known TCF4 binding protein.

It was also confirmed that TCF4 and β-catenin which is its binding protein, undergo immunoprecipitation due to anti-TNIK antibody. These results demonstrated the interaction between TCF4, β-catenin, and TNIK.

Next, the localization of TNIK and TCF4 in DLD-1 cells and HCT-116 cells was studied by the immunofluorescence-stain method.

The result is shown in FIG. 2. Regarding TNIK, mesh-like staining was observed throughout the entire cell (FIG. 2, TNIK), thus confirming that TNIK is present throughout the entire cell. On the other hand, in the case of TCF4, staining was observed in the nucleus (FIG. 2, TCF4), and it was confirmed that TCF4 is localized in the nucleus.

The fact that both TNIK and TCF4 are localized in the nucleus was confirmed by Merge in FIG. 2.

Example 2

(Increase of Transcriptional Activity of β-catenin/TCF4 Complex Due to TNIK)

As mentioned above, TNIK is an enzyme for phosphorylation, and since it can be a drug target, the effect of TNIK on transcription control of β-catenin/TCF4 complex was studied.

pCIneo-HA-TNIK incorporating human TNIK full length cDNA or the 54th lysine at the ATP binding site was replaced by arginine, pCIneo-HA-TNIK K54R incorporating K54R which is a mutant lacking the function of an enzyme for phosphorylation was introduced into DLD-1 cells and HCT-116 cells, and the effect on TCF/LEF reporter activity due to TNIK was examined.

A TCF/LEF luciferase reporter vector (TOP or FOP), pCIneo-HA-TNIK, pCIneo-HA-TNIK K54R, or a control plasmid (pCIneo-HA), was introduced into DLD-1 cells and HCT-116 cells. Next, according to the aforesaid protocol, after 24 hours had elapsed, the luciferase activity was measured 3 times.

The result is shown in FIG. 3. The diagram at the bottom of FIG. 3 are the results of an immunoblot analysis using anti-HA and anti-β-Actin antibodies which showed the protein expression level. It was confirmed that when TNIK was expressed, the firefly luciferase activity of TCF/LEF reporter TOP-FLASH (black column) increases compared with a control vector (pCIneo-HA). However, when TNIK K54R was expressed, an increase of transcriptional activity was not observed. From this result, it was confirmed that the transcription of β-catenin/TCF4 is inhibited by blocking the kinase activity of TNIK To examine the effect of TNIK on transcription control of β-catenin/TCF4 complex, the expression of TNIK was knocked down using RNA interference, and the effect of on the transcriptional activity of β-catenin/TCF4 was examined.

The TCF/LEF luciferase reporter vector (TOP or FOP), two kinds of siRNA (TNIK-12, TNIK-13) with respect to TNIK, and two kinds of control siRNA (X, IX), were introduced into DLD-1 cells and HCT-116 cells. Next, according to the aforesaid protocol, after 48 hours from introduction, the luciferase activity was measured by repeating the experiment 3 times.

The result is shown in FIG. 4. The diagram in the lower part of FIG. 4 is the result of an immunoblot analysis using anti-TNIK and anti-β-Actin antibodies showing the levels of knocked down TNIK and proteins. Due to TNIK knockdown, the luciferase activity fell to about ⅓. From this, it was confirmed that by inhibiting expression of TNIK protein, the transcription of β-catenin/TCF4 can be inhibited.

Next, the effect on cell growth due to this transfection activity was examined by colony formation assay.

pCIneo-HA-TNIK, pCIneo-HA-TNIK K54R, or a control plasmid (pCIneo-HA) was introduced into DLD-1 cells and HCT-116 cells. After 24-hours, G418 was added and the cells were cultured for 8 days. Next, cell proliferation potential was visualized by Gimza staining.

The result is shown in FIG. 5. Cell proliferation increased remarkably due to over expression of TNIK. On the other hand, significant increase of cell proliferation was not observed in the expression test of K54R. From this result, it was confirmed that by impairing the phosphorylating ability of TNIK, cell proliferation is also inhibited.

Further, the expression of TNIK was knocked down using RNA interference (iRNA), and the effect of the knockdown of TNIK on the transcriptional activity of β-catenin/TCF4 was examined.

Three types of shRNA plasmid (TNIK-1, TNIK-2, TNIK-3) for TNIK, or control shRNA, were introduced into DLD-1 cells and HCT-116 cells.

After 24-hours, G418 was added, and the cells were cultured for 8 days. Next, cell proliferation potential was visualized by Gimza staining.

The result is shown in FIG. 6. The diagram on the right of FIG. 6 is the result of an immunoblot analysis showing TNIK and protein levels which were knocked down using anti-TNIK and anti-β-Actin antibodies. As in the case of transcriptional activity, it was confirmed that cell proliferation is remarkably decreased by inhibiting the expression of TNIK. Also from this result, it was confirmed that cell proliferation is inhibited by inhibiting the transfection of β-catenin/TCF4 by TNIK.

Example 3

(Need for Phosphorylation of TCF-4 by TNIK Participating in the Combination of TNIK and TCF4)

Since wild-type TNIK which is an enzyme for phosphorylation, and mutant K54R which lacks phosphorylating ability, control transcription and cell growth in opposite directions respectively, a detailed examination of their functional differences was performed.

First, after expressing wild-type TNIK and mutant K54R in DLD-1 cells, the intracellular location was examined by the immunofluorescence-stain method.

pCIneo-HA-TNIK or pCIneo-HA-TNIK K54R was introduced into the DLD-1 cells.

For TNIK, double immunofluorescence staining was performed using anti-HA rabbit polyclonal antibody, and for TCF4, double immunofluorescence staining was performed using anti-TCF4 monoclonal antibody.

As shown in FIG. 7, in the case of cells which were made to express wild-type TNIK, TNIK was seen to be distributed throughout the entire cell, and a particularly strong expression was observed in the nucleus (FIG. 7, upper left). On the other hand, in the case of the cells which were made to express K54R, expression of K54R was hardly observed in the nucleus (FIG. 7, lower left figure).

Since TCF4 is localized in the nucleus (FIG. 7, upper and lower middle diagrams), wild-type TNIK is the same as TCF4 insofar as it is localized in the nucleus (FIG. 7, upper right diagram). On the other hand, in the case of K54R, it was not observed to be the same as TCF4 in its type of localization (FIG. 7, lower right). From this result, it can be conjectured that the interaction of β-catenin/TCF4 transcription complex and TNIK in the nucleus can be inhibited by blocking the kinase activity of TNIK.

Next, DLD-1 cells and HCT-116 cells were made to express wild-type TNIK and K54R, respectively. Next, the interaction of TNIK and TCF4 was examined by the immunoprecipitation technique using the cell extract liquid extracted from these cells. pCIneo-HA-TNIK, pCIneo-HA-TNIK K54R, or a control plasmid (pCIneo-HA) was introduced into DLD-1 cells and HCT-116 cells.

The cell extract was examined by immunoprecipitation using anti-HA monoclonal antibody, anti-TCF4 monoclonal antibody, or normal mouse IgG (IgG).

On the precipitation (Ab), an immunoblot was performed using anti-HA polyclonal antibody and anti-TCF4 polyclonal antibody.

The result is shown in FIG. 8. The figure in the lower part of FIG. 8 is the result of an immunoblot analysis when using anti-β-Actin antibody which showed the protein level amount. In the case of wild-type TNIK, a strong combination with TCF4 was observed compared with the control, but in the case of K54R, only a weak immunoprecipitation band was observed. From this, it can be conjectured that if the kinase activity of TNIK is blocked, the combination of TNIK and β-catenin/TCF4 complex does not take place.

In order to examine whether these localizations and interactions operate on a functional level, DLD-1 cells were made to express pFLAG-TCF4, the wild-type of TNIK and mutant K54R, and an evaluation of the cell extract was performed by the immunoprecipitation technique using anti-TCF4 antibody.

pFLAG-TCF4 and pCIneo-HA-TNIK, pCIneo-HA-TNIK K54R, or a control plasmid (pCIneo-HA) was introduced into DLD-1 cells. Next, the cell extract was evaluated by the immunoprecipitation technique using anti-TCF4 monoclonal antibody (Ab) or normal mouse IgG (IgG). On the precipitation, an immunoblot was performed using anti-phosphoserine rabbit polyclonal antibody (ab9332) and anti-TCF4 rabbit polyclonal antibody (sc-1 3027). In order to show the expression levels, an immunoblot was performed on total cell lysate using anti-TCF4 monoclonal antibody (6H5-3), anti-HA monoclonal antibody (12CA5), and anti-β-actin monoclonal antibody (AC-74).

The result is shown in FIG. 9. The diagram in the lower part of FIG. 9 shows the result of an immunoblot analysis using anti-TCF4, anti-HA, and anti-β-Actin antibody showing the protein expression levels. When the degree of phosphorylation of TCF4 was examined using anti-phospho serine and anti-phospho threonine antibody when wild-type TNIK was expressed, the serine phosphorylation band of TCF4 was detected. However, when the mutant K54R was expressed, significant serine phosphorylation was not observed compared with control.

Also, phosphorylation of threonine was not observed. This result shows that TNIK phosphorylates at least one serine in the amino acid sequence of TCF4 protein using TCF4 protein as a substrate.

Hence, it is clear that due to the interaction of TNIK with β-catenin/TCF4 complex, the transfection activity of the TCF/LEF family is blocked depending on the expression and enzyme activity of TNIK. From this observation, it appears that the transfection activity of the TCF/LEF family can be blocked using a compound which blocks the kinase activity of TNIK, or a compound which blocks the interaction of TNIK and β-catenin/TCF4 complex, which suggests the possibility of using the compound in cancer prevention or therapy.

INDUSTRIAL APPLICABILITY

The screening method for an anticancer drug of the invention has high effectiveness, and is useful for the development of a therapeutic agent for cancer with few side effects. Since the invention can contribute to the development of an anticancer drug not only for colon cancer, but also for other cancers in which β-catenin participates, such as ovarian cancer and endometrial cancer, it has very great industrial potential.

What is claimed is:

1. A screening method for selecting an anticancer drug effective in cancer in which β-catenin participates, the method comprising the steps of:
   (a) providing a number of candidate compounds;
   (b) measuring the kinase activity of the TRAF2 and NCK interacting kinase in the presence of each candidate compound;
   (c) determining that a candidate compound is an anticancer drug candidate compound when the measured kinase activity in the presence of the candidate compound is lower than kinase activity of TRAF2 and NCK interacting kinase in the absence of the candidate compound; and
   (d) selecting an anticancer drug from among the candidate compounds determined to be anticancer drug candidate compounds.

2. The screening method for an anticancer drug according to claim 1, wherein the candidate compound blocks the kinase activity of the TRAF2 and NCK interacting kinase by interfering with binding of ATP to the ATP binding site of the TRAF2 and NCK interacting kinase.

3. The screening method for an anticancer drug according to claim 1, wherein the cancer is selected from the group consisting of colon cancer, ovarian cancer, endometrial cancer, childhood brain tumor, liver cancer, hepatoblastoma and stomach cancer.

4. The screening method for an anticancer drug according to claim 1, wherein, in step (a) the number of candidate compounds consists of compounds that can conform to an ATP binding site of the TRAF2 and NCK interacting kinase.

5. A screening method for selecting an anticancer drug effective in cancer in which β-catenin participates, the method comprising the steps of:
   (a) providing a number of candidate compounds;
   (b) measuring a degree of interaction between the TRAF2 and NCK interacting kinase and the β-catenin/T-cell factor-4 transcription complex in the presence of each candidate compound;
   (c) determining that a candidate compound is an anticancer drug candidate compound when the measured degree of interaction in the presence of the candidate compound is less than a degree of interaction between TRAF2 and NCK interacting kinase and a β-catenin/T-cell factor-4 transcription complex in the absence of the candidate compound; and
   (d) selecting an anticancer drug from among the candidate compounds determined to be anticancer drug candidate compounds.

6. The screening method for an anticancer drug according to claim 5, wherein the degree of interaction between the TRAF2 and NCK interacting kinase and the β-catenin/T-cell factor-4 transcription complex either in the presence of the candidate compound or in the absence of the candidate compound is measured using a two-hybrid assay.

7. The screening method for an anticancer drug according to claim 5, wherein the degree of interaction between the TRAF2 and NCK interacting kinase and the β-catenin/T-cell factor-4 transcription complex either in the presence of the candidate compound or in the absence of the candidate compound is measured using an antigen-antibody reaction.

8. The screening method for an anticancer drug according to claim 5, wherein the degree of interaction between the TRAF2 and NCK interacting kinase and the β-catenin/T-cell factor-4 transcription complex in the presence of the candidate compound is measured by culturing cells expressing the TRAF2 and NCK interacting kinase, the β-catenin, and the T-cell factor-4 in the presence of the candidate compound, and wherein the candidate compound is determined to be an anticancer drug when cell proliferation of the cultured cells in the presence of the candidate compound is inhibited compared to cell proliferation when cells expressing the TRAF2 and NCK interacting kinase, the β-catenin, and the T-cell factor-4 are cultured in the absence of the candidate compound.

9. The screening method for an anticancer drug according to claim 5, wherein the cancer is selected from the group consisting of colon cancer, ovarian cancer, endometrial cancer, childhood brain tumor, liver cancer, hepatoblastoma and stomach cancer.

* * * * *